US008491644B1

(12) United States Patent
Carson et al.

(10) Patent No.: US 8,491,644 B1
(45) Date of Patent: Jul. 23, 2013

(54) PORTABLE, REFRIGERANT-BASED APPARATUS AND METHOD FOR RAPID SYSTEMIC PATIENT COOLING

(75) Inventors: Gary Carson, Golden, CO (US); Gary Gruzecki, Golden, CO (US); Steve Whitehead, Arvada, CO (US)

(73) Assignee: Medivance Incorporated, Louisville, CO (US)

( * ) Notice: Subject to any disclaimer, the term of this patent is extended or adjusted under 35 U.S.C. 154(b) by 1160 days.

(21) Appl. No.: 11/360,021

(22) Filed: Feb. 21, 2006

Related U.S. Application Data (60) Provisional application No. 60/654,929, filed on Feb. 22, 2005.

(51) Int. Cl.
*A61F 7/00* (2006.01)
(52) U.S. Cl.
USPC .......................................................... 607/104
(58) Field of Classification Search
USPC ..................................... 607/104–106; 165/46
See application file for complete search history.

(56) References Cited

U.S. PATENT DOCUMENTS

| | | | | |
|---|---|---|---|---|
| 2,575,325 A | * | 11/1951 | Ambrose et al. ................. | 62/181 |
| 3,007,473 A | | 11/1961 | Jackson et al. ................. | 128/400 |
| 3,064,649 A | | 11/1962 | Fuson ............................ | 128/214 |
| 3,074,410 A | | 1/1963 | Foster ........................... | 128/400 |
| 3,460,538 A | | 8/1969 | Armstrong ................. | 128/303.1 |
| 3,504,674 A | * | 4/1970 | Negrin et al. ................. | 607/105 |
| 3,625,279 A | | 12/1971 | Mayo ............................... | 165/62 |
| 3,744,555 A | | 7/1973 | Fletcher et al. ................. | 165/46 |
| 3,869,871 A | * | 3/1975 | Rybalko et al. ................. | 62/178 |
| 3,888,259 A | | 6/1975 | Miley ............................ | 128/400 |
| 3,894,213 A | | 7/1975 | Agarwala ....................... | 219/297 |
| 3,995,621 A | | 12/1976 | Fletcher et al. .................... | 128/2 |
| RE29,438 E | * | 10/1977 | MacCracken et al. .......... | 165/46 |
| 4,118,946 A | | 10/1978 | Tubin ............................. | 62/514 |
| 4,149,529 A | | 4/1979 | Copeland et al. ............. | 128/24.1 |
| 4,170,998 A | * | 10/1979 | Sauder .......................... | 607/104 |
| 4,172,454 A | * | 10/1979 | Warncke et al. .......... | 128/201.29 |
| 4,184,537 A | * | 1/1980 | Sauder ............................ | 165/46 |
| T994001 I4 | | 5/1980 | Buckberg et al. ............. | 128/214 |
| 4,259,961 A | | 4/1981 | Hood, III ....................... | 128/400 |
| 4,307,578 A | * | 12/1981 | Ecker ........................... | 62/238.6 |
| 4,416,280 A | | 11/1983 | Carpenter et al. ............. | 128/399 |
| 4,427,009 A | | 1/1984 | Wells et al. ................... | 128/400 |
| 4,459,468 A | | 7/1984 | Bailey ........................... | 219/490 |
| 4,466,438 A | * | 8/1984 | Katz .............................. | 607/105 |
| 4,508,123 A | | 4/1985 | Wyatt et al. ................... | 128/692 |
| 4,512,163 A | | 4/1985 | Wells et al. ..................... | 62/394 |

(Continued)

FOREIGN PATENT DOCUMENTS

WO    WO 03030790 A1 *  4/2003

*Primary Examiner* — Linda Dvorak
*Assistant Examiner* — Kaitlyn Smith
(74) *Attorney, Agent, or Firm* — Marsh Fischmann & Breyfogle LLP (57) ABSTRACT

A portable patient cooling apparatus is provided that includes a self-contained refrigerator and on-board power storage supply for stand alone operation. The apparatus is interconnectable to one or more heat exchange devices (e.g. patient contact pads or intravascular catheters) through which a cooled fluid may be circulated for patient cooling. Such fluid may be liquid contained within a reservoir comprising the apparatus during periods of non-use. The apparatus preferably defines a total volume of less than about 0.04 m³, while having a total weight of less than about 15 kg to yield a total circulated fluid cooling capacity of at least 200 watts.

46 Claims, 8 Drawing Sheets

U.S. PATENT DOCUMENTS

| | | | | |
|---|---|---|---|---|
| 4,523,594 A | 6/1985 | Kuznetz | | 128/402 |
| 4,691,762 A | 9/1987 | Elkins et al. | | 165/46 |
| 4,844,072 A | 7/1989 | French et al. | | 128/400 |
| 4,951,665 A | 8/1990 | Schneider | | 128/400 |
| 4,962,761 A | 10/1990 | Golden | | 128/400 |
| 4,966,145 A | 10/1990 | Kikumoto et al. | | 128/377 |
| 4,982,736 A | 1/1991 | Schneider | | 128/400 |
| 5,033,136 A | 7/1991 | Elkins | | 5/421 |
| 5,051,562 A | 9/1991 | Bailey et al. | | 219/494 |
| 5,097,829 A | 3/1992 | Quisenberry | | 128/400 |
| 5,266,778 A | 11/1993 | Bailey | | 219/497 |
| 5,270,005 A | 12/1993 | Raible | | 422/46 |
| 5,332,884 A | 7/1994 | Bailey | | 219/494 |
| 5,333,677 A * | 8/1994 | Molivadas | | 165/272 |
| 5,344,436 A * | 9/1994 | Fontenot et al. | | 607/104 |
| 5,386,823 A * | 2/1995 | Chen | | 128/204.15 |
| 5,411,541 A | 5/1995 | Bell et al. | | 607/104 |
| 5,456,701 A | 10/1995 | Stout | | 607/104 |
| D364,680 S | 11/1995 | Dye | | D24/129 |
| 5,466,216 A | 11/1995 | Brown et al. | | 604/33 |
| 5,470,353 A | 11/1995 | Jensen | | 607/104 |
| 5,507,792 A | 4/1996 | Mason et al. | | 607/104 |
| 5,573,502 A | 11/1996 | LeCocq et al. | | 604/4 |
| 5,609,571 A | 3/1997 | Buckberg et al. | | 604/4 |
| 5,609,620 A | 3/1997 | Daily | | 607/105 |
| 5,634,940 A | 6/1997 | Panyard | | 607/104 |
| 5,643,191 A | 7/1997 | Buckberg et al. | | 604/4 |
| 5,645,531 A | 7/1997 | Thompson et al. | | 604/67 |
| 5,702,358 A | 12/1997 | Witherspoon et al. | | 604/4 |
| 5,709,654 A * | 1/1998 | Klatz et al. | | 604/24 |
| 5,730,720 A | 3/1998 | Sites et al. | | 604/27 |
| 5,733,320 A | 3/1998 | Augustine | | 607/107 |
| 5,817,045 A | 10/1998 | Sever, Jr. | | 604/4 |
| 5,862,675 A * | 1/1999 | Scaringe et al. | | 62/196.3 |
| 5,865,841 A | 2/1999 | Kolen et al. | | 607/104 |
| 5,871,526 A | 2/1999 | Gibbs et al. | | 607/104 |
| 5,895,418 A * | 4/1999 | Saringer | | 607/104 |
| 5,957,137 A | 9/1999 | Dalke et al. | | 128/898 |
| 5,957,879 A | 9/1999 | Roberts et al. | | 604/4 |
| RE36,386 E | 11/1999 | Abott et al. | | 604/4 |
| 5,980,561 A | 11/1999 | Kolen et al. | | 607/104 |
| 5,989,238 A * | 11/1999 | Ginsburg | | 604/500 |
| 5,989,285 A | 11/1999 | DeVilbiss et al. | | 607/107 |
| 5,997,816 A | 12/1999 | McIntosh et al. | | 422/44 |
| 6,019,783 A | 2/2000 | Philips et al. | | 607/104 |
| 6,033,432 A | 3/2000 | Augustine et al. | | 607/96 |
| 6,042,559 A | 3/2000 | Dobak, III | | 604/7 |
| 6,086,609 A * | 7/2000 | Buckley | | 607/104 |
| 6,095,992 A | 8/2000 | Augustine | | 602/2 |
| 6,110,139 A | 8/2000 | Loubser | | 604/30 |
| 6,149,674 A | 11/2000 | Borders | | 607/96 |
| 6,182,453 B1 * | 2/2001 | Forsberg | | 62/125 |
| 6,197,045 B1 * | 3/2001 | Carson | | 607/104 |
| 6,238,427 B1 | 5/2001 | Matta | | 607/104 |
| 6,254,626 B1 | 7/2001 | Dobak, III et al. | | 607/105 |
| 6,261,312 B1 | 7/2001 | Dobak, III et al. | | 607/105 |
| 6,572,640 B1 * | 6/2003 | Balding et al. | | 607/105 |
| 6,581,403 B2 * | 6/2003 | Whitebook et al. | | 62/434 |
| 6,620,189 B1 * | 9/2003 | Bloom et al. | | 607/106 |
| 6,692,518 B2 * | 2/2004 | Carson | | 607/104 |
| 6,699,267 B2 * | 3/2004 | Voorhees et al. | | 607/104 |
| 6,878,156 B1 | 4/2005 | Noda | | 607/106 |
| 6,899,103 B1 * | 5/2005 | Hood et al. | | 128/845 |
| 6,962,601 B2 * | 11/2005 | Becker et al. | | 607/105 |
| 6,991,645 B2 * | 1/2006 | Dobak | | 607/105 |
| 7,004,960 B2 * | 2/2006 | Daoud | | 607/105 |
| 7,101,388 B2 * | 9/2006 | Noda et al. | | 607/105 |
| 7,318,834 B2 * | 1/2008 | Njemanze | | 607/105 |
| 7,640,764 B2 * | 1/2010 | Gammons et al. | | 62/259.3 |
| 2001/0039439 A1 * | 11/2001 | Elkins et al. | | 607/104 |
| 2003/0149401 A1 * | 8/2003 | Benetti Diaz De Brito et al. | | 604/113 |
| 2004/0133135 A1 * | 7/2004 | Diana | | 601/152 |
| 2004/0260369 A1 * | 12/2004 | Schock et al. | | 607/104 |
| 2005/0027281 A1 * | 2/2005 | Lennox | | 604/508 |
| 2005/0177212 A1 * | 8/2005 | Njemanze | | 607/104 |
| 2006/0030915 A1 * | 2/2006 | Lennox et al. | | 607/104 |
| 2006/0076379 A1 * | 4/2006 | Hussaini et al. | | 224/275 |
| 2006/0235496 A1 * | 10/2006 | Collins et al. | | 607/96 |
| 2007/0203552 A1 * | 8/2007 | Machold et al. | | 607/104 |
| 2007/0244434 A1 * | 10/2007 | Noda et al. | | 604/113 |
| 2008/0082029 A1 * | 4/2008 | Diana | | 601/152 |
| 2008/0228248 A1 * | 9/2008 | Guyuron et al. | | 607/108 |
| 2008/0269676 A1 * | 10/2008 | Bieberich et al. | | 604/113 |
| 2009/0043256 A1 * | 2/2009 | Landy et al. | | 604/113 |
| 2009/0131835 A1 * | 5/2009 | Voorhees et al. | | 600/595 |
| 2010/0071130 A1 * | 3/2010 | Frias | | 5/421 |
| 2010/0084125 A1 * | 4/2010 | Goldstein et al. | | 165/287 |
| 2010/0106229 A1 * | 4/2010 | Gammons et al. | | 607/104 |
| 2010/0121273 A1 * | 5/2010 | Kochanek et al. | | 604/113 |
| 2010/0137951 A1 * | 6/2010 | Lennox et al. | | 607/104 |
| 2010/0204765 A1 * | 8/2010 | Hall et al. | | 607/105 |
| 2011/0077557 A1 * | 3/2011 | Wing et al. | | 601/2 |
| 2011/0106023 A1 * | 5/2011 | Lowe | | 604/291 |
| 2012/0036869 A1 * | 2/2012 | Kim et al. | | 62/3.4 |

* cited by examiner

PORTABLE, REFRIGERANT-BASED APPARATUS AND METHOD FOR RAPID SYSTEMIC PATIENT COOLING

CROSS-REFERENCE TO RELATED APPLICATIONS

This application claims priority under 35 U.S.C. §119 to prior U.S. Provisional Patent Application No. 60/654,929, filed Feb. 22, 2005, entitled "PORTABLE, REFRIGERANT-BASED APPARATUS AND METHOD FOR RAPID SYSTEMIC PATIENT COOLING," the entire contents of which are incorporated herein as if set forth herein in full.

FIELD OF THE INVENTION

The present invention generally relates to a portable apparatus and related method for rapid systemic cooling of a patient via contact thermal exchange. The invention is particularly apt for treating stroke and head trauma patients.

BACKGROUND OF THE INVENTION

The use of contact pads for systemic cooling and/or heating bodily tissue is known. In such systems a fluid, e.g. water or air, is circulated through one or more pads to affect surface-to-surface thermal energy exchange with a patient. Highly effective contact pads and related systems and componentry include those disclosed in U.S. Pat. Nos. 6,375,674, 6,645,232, 6,827,728, 6,669,715 and 6,802,855, 6,818,012, hereby incorporated by reference in their entirety.

The therapeutic use of such systemic cooling systems is ever-expanding. Of particular interest, it is now accepted that rapid systemic cooling of stroke, cardiac arrest and head trauma patients can yield significant therapeutic benefits. In this regard, research indicates that even though a stroke or cardiac arrest victim's brain cells may lose their ability to function, the cells do not necessarily die quickly. In fact, brain damage from a stroke or cardiac arrest may take hours to reach maximum effect. Neurologic damage may be reduced and the stroke or cardiac arrest victim's outcome improved if a neuroprotectant therapy is applied within this time frame.

Similarly, elements in the genesis of traumatic brain injury (e.g. resulting from falls, vehicular accidents and the like) are now understood to overlap with elements in the genesis of neurologic damage in stroke victims. In particular, delayed secondary injury at the cellular level after the initial head trauma event is now recognized as a major contributing factor to the ultimate tissue loss that occurs after brain injury. Again, neurologic damage may be reduced if a neuroprotectant therapy is rapidly applied.

Further in this regard, studies have shown that treatment with mild hypothermia, defined as lowering core body temperature by 2-3° C., confers neuroprotection in stroke victims, and may hasten neurologic recovery and improve outcomes when applied for twenty-four to seventy-two hours in cases of traumatic head injury. Again, to optimize such therapies, the neuroprotective bodily occurring should be initiated as soon as possible after a stroke or traumatic head injury.

As these and other medical applications for systemic cooling have continued to evolve, the present inventors have recognized the desirability of enhancing the portability of patient cooling systems so that patient treatment may be promptly initiated. More particularly, while known heating/cooling contact pad systems have proven effective for many applications, the present inventors have recognized that additional emergency-oriented applications can be realized via the implementation of further-improved liquid cooling methodologies and stand-alone componentry, as well as enhanced componentry packaging.

SUMMARY OF THE INVENTION

In view of the foregoing, one objective of the present invention is to provide a patient cooling apparatus and method that provides, enhanced, rapid-cooling capabilities, while also yielding size, weight and operating efficiencies.

In the later regard, a related objective of the present invention is to provide an improved patient cooling apparatus that is well-adapted for portable applications, including in particular utilization in emergency, patient transport vehicles.

The above-noted objectives and additional advantages are realized in the present invention. To do so, a cooling apparatus is provided that comprises a self-contained refrigerator for rapid fluid cooling and an on-board power storage supply for stand-alone operation. Further, the cooling apparatus is of reduced size and weight. As a result, the invention is particularly well-suited for portable use in emergency, patient transport vehicles.

More particularly, the inventive portable cooling apparatus may comprise a reservoir containing a fluid, and a circulating pump fluidly interconnected to the reservoir for circulating the fluid through at least one patient heat exchange device interconnectable to the apparatus. Such patient heat exchange device(s) may comprise at least one of an external patient contact device for heat exchange via direct contact with an external tissue surface, and an internal patient contact device for exchange via direct contact with an internal tissue surface and/or bodily fluid (e.g. a catheter for intravascular contact).

The apparatus may further include a heat exchanger, fluidly interconnected with the circulating pump and reservoir, for cooling the circulated fluid and for receiving a refrigerant that is circulated by the self-contained refrigerator to affect cooling of the circulated fluid. As noted, an onboard power storage supply is also included to provide electrical power to the circulating pump, refrigerator and other componentry during independent, stand-alone operation of the apparatus (e.g. during patient transport).

In one aspect of the invention, the portable apparatus may be provided to yield a circulated fluid cooling capacity of at least about 200 watts (e.g. with a circulated fluid temperature of about 10° C. or less). More preferably, a circulated fluid cooling capacity of between about 300 watts to 600 watts may be realized (e.g. with a circulated fluid temperature of at least about 10° C. or less).

In another aspect of the present invention, the apparatus may comprise at least one patient heat exchanger device, fluidly interconnectable with the reservoir, circulating pump and heat exchanger, for contacting a patient. Preferably, the cooling fluid circulated through the patient heat exchanger device(s) may cool a patient at a rate of at least about 1.0 C/hr. Even more preferably, the apparatus may be provided so that the circulated fluid yields a patient cooling rate of between about 1.5 C/hr to 4.0 C/hr.

To realize such patient cooling rates utilizing a fluidly interconnectable patient contact pad(s), it is preferable for the contact pad(s) to include an adhesive surface for contacting a patient's skin, wherein thermal exchange is realized through the adhesive surface with a fluid circulation layer through which the circulated fluids flows. In one approach, the adhesive surface may be defined by an outer surface of an unformable layer that comprises a first material (e.g. a conductive fluid) suspended in a matrix deferred by a second material (e.g. a polymeric material), such as a hydrogel. Further, it is preferable for the apparatus to be arranged so that the circulating pump is interconnectable to the patient contact pad(s) so as to draw the circulated fluid through the patient contact pad(s) under negative pressure.

In another aspect of the present invention, the apparatus componentry is arranged so that the total volume defined thereby is less than about 0.04 m³. Even more preferably, the apparatus defines a total volume of between about 0.01 m³ and 0.02 m³. Relatedly, the total volume preferably has a maximum width dimension of less than about 9 inches, and more preferably between about 4 and 7 inches; a maximum height dimension of less than about 15 inches, and more preferably between about 6 and 11 inches; and a maximum length dimension of less than about 16 inches, and more preferably between about 9 and 14 inches. As may be appreciated, an apparatus having components arranged within the total volume and dimensional ranges specified above accommodates ready placement relative to patient transport devices, such as gurneys and the like within emergency transport vehicles (e.g. helicopters, ambulances, etc.).

In a related aspect, the power supply of the portable apparatus may be provided to comprise less than about 12% of the total volume of the apparatus, and more preferably, between about 8% and 12% of the total volume. Further, the reservoir may be provided to comprise less than about 16% of the total volume, and more preferably between about 8% and 16% of the total volume.

To enhance stability and realize compactness, the power supply is preferably located in a bottom layer of the total volume, while the reservoir and refrigerator are located in side-by-side relation in an intermediate layer of the total volume that overlies the bottom layer. Further, the heat exchanger is preferably located in a fluid circulation layer of the total volume that overlies the intermediate layer. Additional componentry may also be located in the fluid circulation layer, including for example a flow meter for measuring a flow rate of the circulated fluid and providing an output signal relating thereto for use in control of the circulating pump, and a heater for heating the circulated fluid. In this regard, the refrigerator may be operated in a steady-state manner to provide a relatively constant cooling influence, while the circulating pump may be controllable (e.g. the speed/throughput fluid flow rate) to achieve a desired rate of patient cooling. Relatedly, the heater may be employed for rapid, fine-tuned adjustment of the temperature of the circulated fluid. Further, the portable apparatus may include a first liquid temperature sensor, located downstream of the heater and upstream of an interconnectable patient contact pad(s), for sensing the temperature of the circulated fluid and providing an output signal relating thereto. Additionally, the apparatus may include a second liquid temperature sensor, located upstream of the heater and downstream of the interconnectable patient contact pad(s), for sensing the temperature of the circulated fluid and providing an output signal relating thereto. As may be appreciated, either or both of the sensed temperature output signals, as well as the flow meter output signal, may be employed to control operation of the above-noted fluid heater and/or circulating pump. Such temperature sensors may also be located in the noted fluid circulation layer.

In addition to the heat exchanger, flow meter, heater, and temperature sensors noted above, inlet and outlet ports for the reservoir and inlet and outlet ports of the circulating pump may also be advantageously disposed in the fluid circulation layer. As may be appreciated, location of such componentry in the fluid circulation layer reduces the length of the fluid circulation path (e.g. the path along which fluid flows from component to component) through the portable apparatus, thereby enhancing compactness and operating efficiencies. In the latter regard, and by way of example, pressure drops downstream of the circulating pump may be reduced. Correspondingly, tubing lines between the various componentry through which the fluid circulates may be reduced or even eliminated, wherein the fluid flows directly between the various components.

Various user interface, processor, electrical circuit and other control componentry may be provided for receiving measurement signals from and providing control signals to the above-noted fluid-circulation-related components, including the circulatory pump, heater, flow meter and temperature sensors. Such control componentry may be located in a top layer overlying the fluid circulation layer. As may be appreciated, the adjacent positioning of the noted fluid-circulation-related components and control components in the fluid circulation layer and top layer, respectively, facilitates overall compactness while also simplifying assembly and servicing.

In relation to the bottom, intermediate fluid circulation and top layers referenced above, the apparatus may be provided so that the bottom layer defines between about 8% and 12% of the total volume of the apparatus, the intermediate layer defines between about 50% and 70% of the total volume, the fluid circulation layer defines between about 10% and 20% of the total volume, and the top layer defines between about 10% and 20% of the total volume.

In a further aspect of the present invention, the refrigerator may include at least one condenser and at least one compressor pump for circulating the refrigerant through the condenser and heat exchanger. Further, at least one fan may be utilized to circulate ambient air past the condenser. Preferably, the refrigerator includes a plurality condensers, wherein first and second condensers may be located on opposing first and second sides at one end of the apparatus, and wherein the fan is located at the same end of the apparatus to circulate ambient air between and past the first and second condensers (e.g. through a fin and tube type condenser). As may be appreciated, such an arrangement facilitates an apparatus having a total volume and dimensional parameters as noted above.

In a further related aspect, the reservoir may be at least partially disposed and supported within a top recess of the reservoir. That is, the circulating pump may be at least partially "nested" within the recess formed in the top of the reservoir so as to yield further space savings. Preferably, the recess is shaped to mattingly receive a coincidentally-shaped portion of the circulating pump.

In yet a further aspect of the invention, the portable apparatus may be provided so that, prior to interconnection with an interconnectable patient contact pad(s), the apparatus has a total weight of less than about 15 kg. Even more preferably, the apparatus may be provided with a total weight of between about 7 kg and 12 kg. Such total weight may be realized with the reservoir being filled with no more than about 2 liter of a liquid (e.g. no more than 2 kg. of water). In this regard, a liquid amount of between about 1.2 liter and 2 liter is preferred (e.g. about 1.2 kg. to 2.0 kg. of water).

Further, a total weight of between about 7 kg. to 12 kg. may be realized with an onboard power storage supply having a weight of less than about 3.5 kg. (e.g. for about 90 minutes of stand-alone operation), and preferably a weight of between about 1.17 kg. and 2.34 kg (e.g. for about 30 to 60 minutes of stand-alone operation). Such capability yields a compact and highly efficient portable apparatus.

In view of the foregoing, it may be recognized that the portable apparatus of the invention may be provided to have a circulated liquid cooling capacity of at least about 0.005 watts (e.g. with a circulated liquid temperature of about 10° C. or less)/cm$^3$ at a weight of less than 0.375 g/cm$^3$. Even more preferably the portable apparatus may be provided to have circulated liquid cooling capacity of between about 0.015 watts to 0.03 watts (e.g. with a circulated liquid temperature of about 10° C. or less)/cm$^3$ at a weight of about 0.35 g/cm$^3$ to 0.6 g/cm$^3$.

As may be appreciated, the present invention also provides a method for cooling a patient that comprises the steps of interconnecting a portable cooling apparatus to a patient heat exchange device, contacting a patient with the patient heat exchange device, and transporting the patient, patient heat exchange device and portable cooling apparatus from a first location (e.g. an emergency site) to a second location (e.g. a medical care facility) during the interconnecting and contacting steps. Of importance, the method further includes the step of utilizing the portable cooling apparatus to cool a fluid and circulate the cooled fluid through the patient heat exchange device in a closed-looped manner during at least a portion of the transporting step.

In one aspect, the portable cooling apparatus may comprise a circulating pump, a heat exchanger fluidly interconnected with the circulating pump, and a self-contained refrigerator as described above. In turn, utilization of the portable cooling apparatus in the method may include the sub-steps of controlling the circulating pump to circulate the fluid through the heat exchanger and patient heat exchange device, and operating the refrigerator to circulate a refrigerant through the heat exchanger to affect cooling of the circulated fluid.

In conjunction with the noted aspect, the portable cooling apparatus may further include a reservoir for containing the circulated fluid, wherein the method may further include the step of storing the fluid in the reservoir during non-use of the portable cooling apparatus. Additionally, the method control of the circulating pump may include the substep of flowing the circulated fluid in to and out of the reservoir during operation of the portable cooling apparatus.

In further relation to the noted aspect, the circulating pump may be operated so as to draw the fluid through the patient heat exchange device at a negative pressure. For example, by locating the inlet port of the circulating pump immediately downstream of an outlet port of the patient heat exchange device, a negative pressure may be established through the patient heat exchange device.

In a related aspect of the inventive method, the portable cooling apparatus may comprise a power storage supply. In turn, the method may further include the step of employing the power storage supply to independently power the circulating pump and self-contained refrigerator to complete at least a portion of the above-noted pump control and refrigerator operation steps. As may be appreciated, such capability is of particular merit, since patient cooling may be continuously provided during portions of a patient transport procedure when no external power source is available. In this regard, the power storage supply may be provided so that it may power the portable cooling apparatus for at least about 20 minutes, and preferably from between about 30 and 60 minutes.

In an additional aspect of the inventive method, the portable cooling apparatus may comprise a heater, fluidly interconnected with the circulating pump downstream of the heat exchanger. In turn, the method may further comprise the steps of controlling the heater to affect heating of the circulated fluid (e.g. for fine-tune fluid temperature control). In this regard, the portable apparatus may include at least one temperature sensor for sensing a temperature of the circulated fluid and providing a corresponding output signal, and an input for receiving a measured patient temperature signal. Further, a processor may be include for utilizing the noted output signal and measured patient temperature signal to control operation of the circulating pump, refrigerator, and heater.

In a simplified arrangement, the refrigerator may be implemented so as to provide a substantially constant rate of fluid cooling when is operated. In turn, the method may further comprise the step of processing the measured patient temperature signal and output signal at the processor to provide control signals, to the circulating pump and heater so as to establish and maintain a desired patient temperature.

In yet a further aspect of the inventive method, the method may provide for either externally contacting a patient with a patient heat exchange device and/or internally contacting a patient heat exchange device with bodily tissue and/or bodily fluid of a patient. In external patient heating applications, the patient heat exchange device may comprise at least one patient contact pad, wherein the method may include the step of adhering a surface of the patient contact pad to a patient's skin so as to affect thermal exchange across the adhesive surface between patient and fluid circulated through the pad. When an internal cooling approach is utilized, the heat exchange device may comprise a catheter, wherein the method may further include the step of inserting the catheter into the patient, e.g. intravascularlly.

As may be appreciated, transport of a patient in the inventive method may include the steps of positioning the patient in an emergency transport vehicle, and locating the portable cooling apparatus adjacent to the patient. In the later regard, the portable cooling apparatus may be provided so that the method may also include the step of completing at least one medical procedure on the patient by medical care personnel with the portable cooling apparatus located in between the patient and the medical care personnel. In this regard, and as noted above, a portable cooling apparatus may be employed that has a total volume of less than about 0.04 m$^3$, and more preferably between about 0.01 m$^3$ and 0.02 m$^3$.

Additional features and advantages of the present invention will be apparent upon consideration of the further description that follows.

DETAILED DESCRIPTION OF THE INVENTION

FIGS. 1-7 illustrate one embodiment of the present invention. Such embodiment provides for circulation of a cooled liquid through a set of external patient contact pad(s). As will be appreciated, various features of the illustrated embodiment may be implemented in other embodiments within the scope of the present invention, including for example embodiments which provide for the circulation of a cooled fluid other than a liquid through and/or which provide for the use of an internal patient contact device such as an intravascular catheter.

Figure 1:
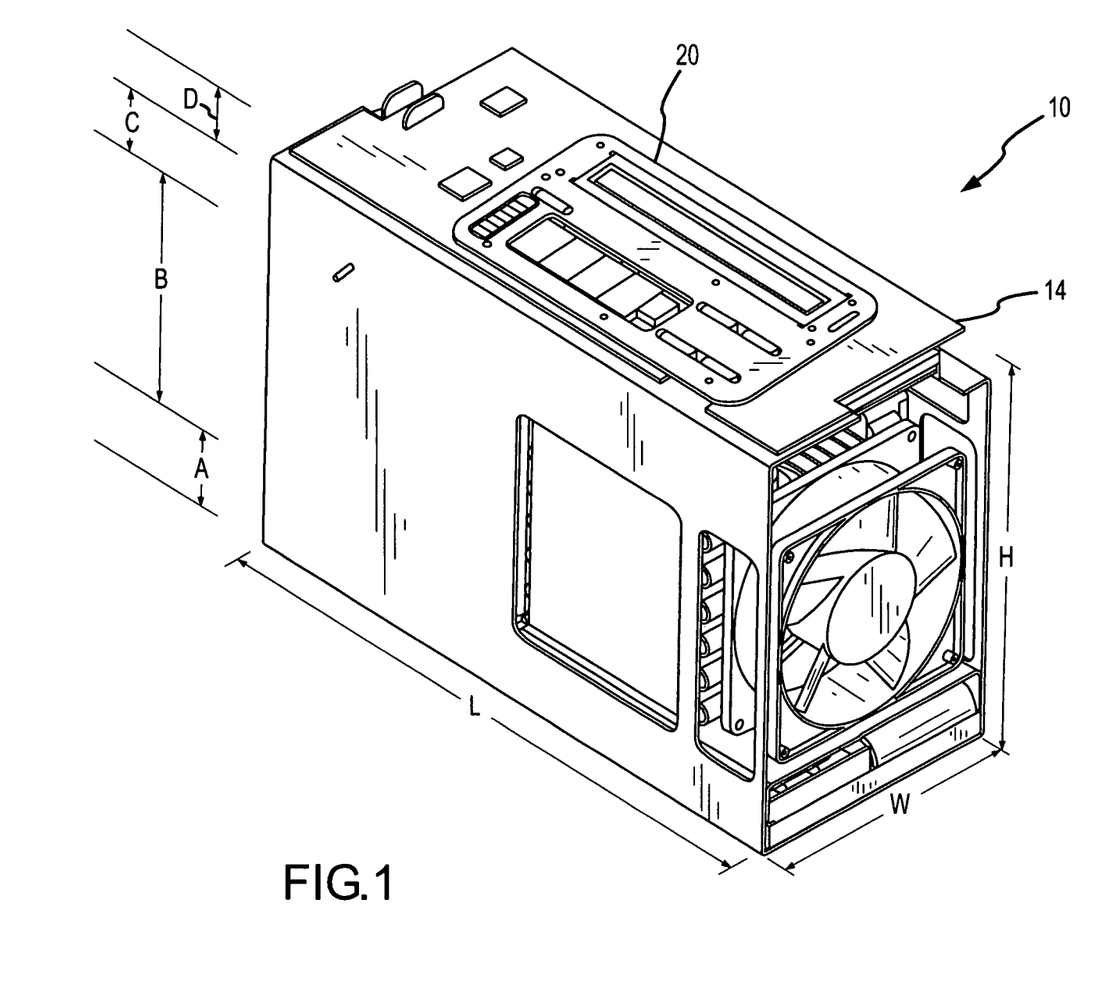
FIG. 1 is a perspective view of one embodiment of a portable apparatus of the present invention.

As shown in FIG. 1, the portable apparatus may include an external housing 12 and top panel 14. Further, top panel 14 may carry a user interface 20 for controlling operation of the apparatus. In the latter regard, one or more processors and electrical circuit componentry may be mounted on an underside of top panel 14.

Figure 2:
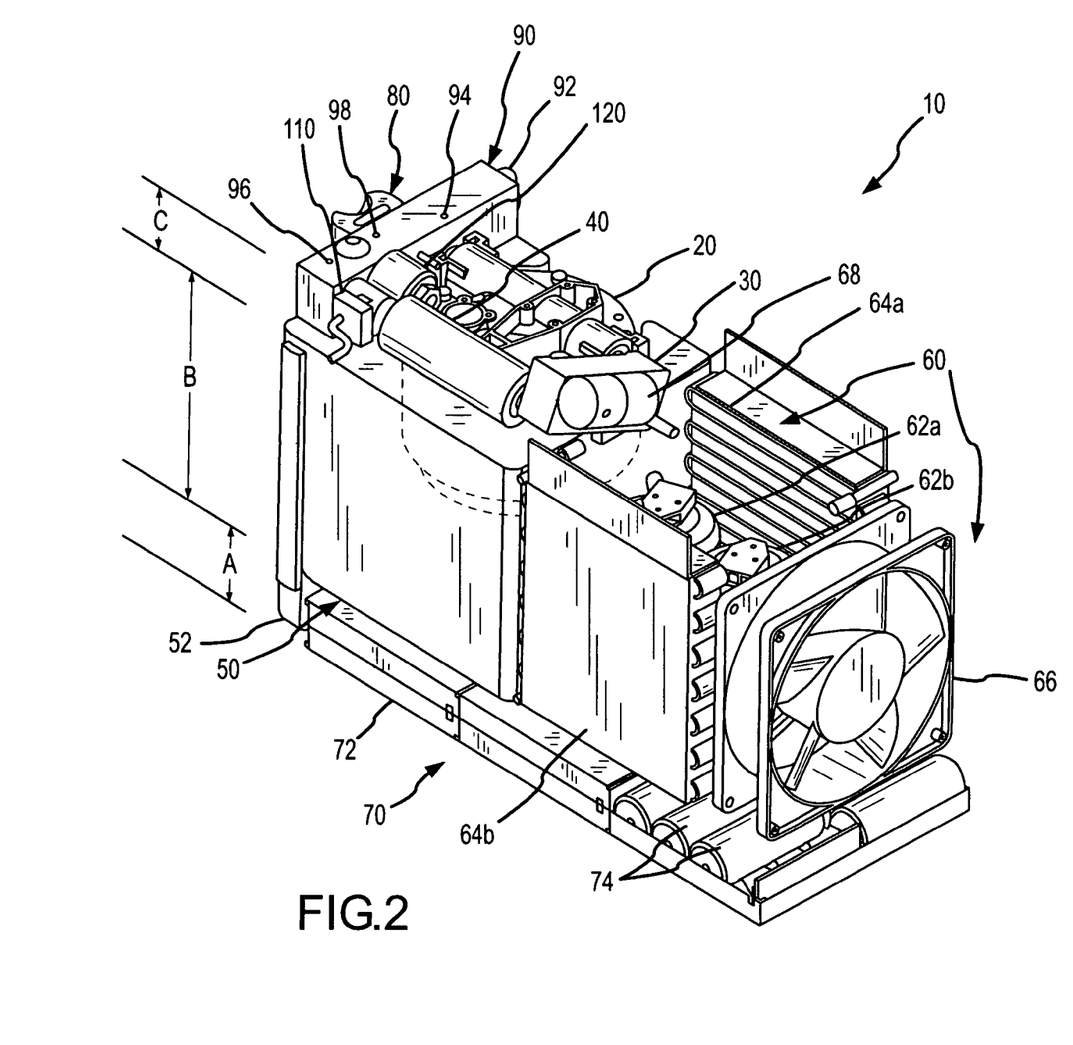
FIG. 2 is a perspective view of the portable apparatus embodiment of FIG. 1, illustrated without external componentry to show internal componentry thereof.
Figure 3:
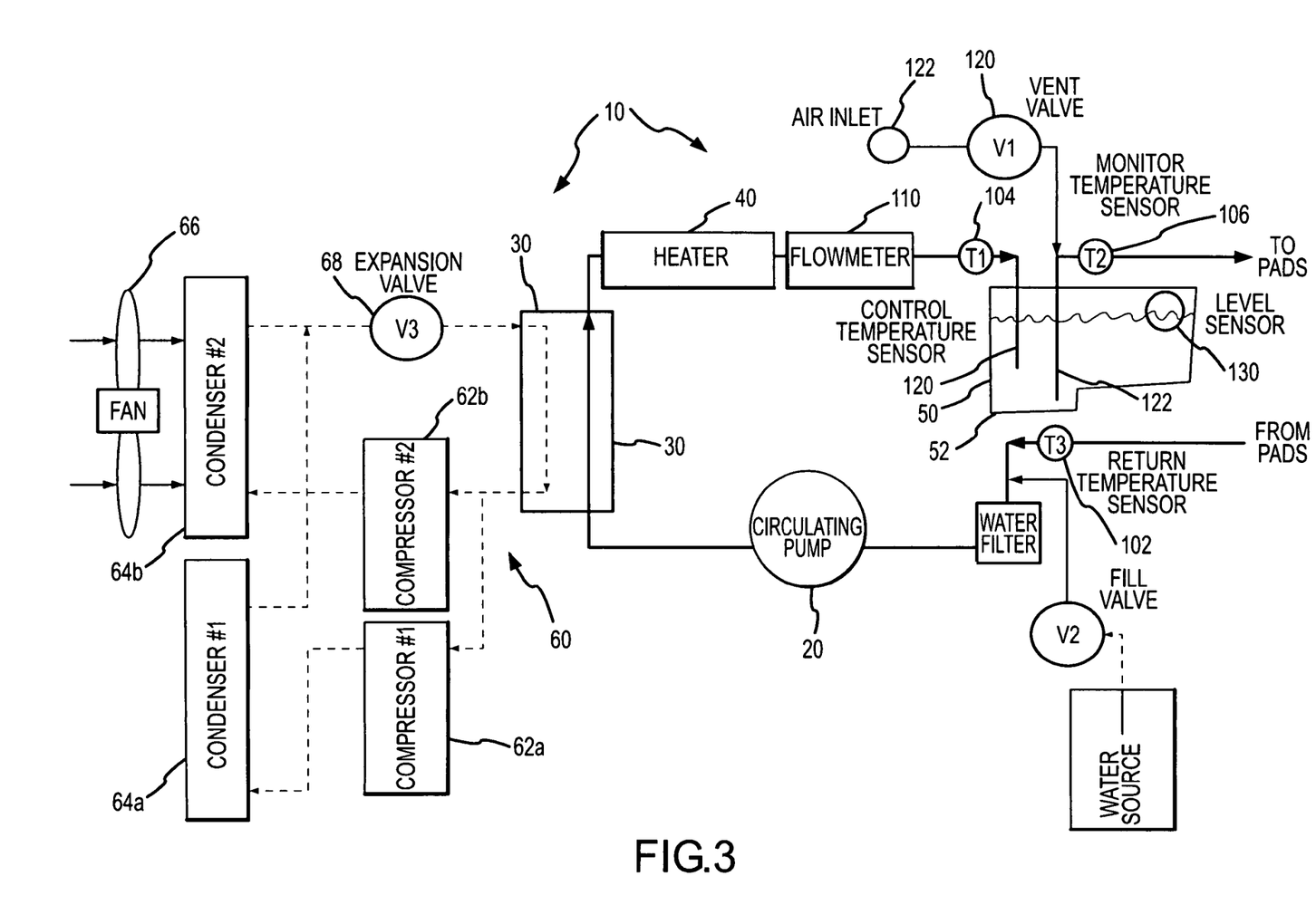
FIG. 3 is a hydraulic schematic illustrating a liquid cooling circuit and a refrigerant circuit of the portable apparatus embodiment of FIGS. 1 and 2.

Referring to FIGS. 2 and 3, the portable apparatus 10 includes a liquid circuit defined by a circulating pump 20, a heat exchanger 30 for cooling the circulated liquid, a heater 40 for heating the circulated liquid, and a reservoir 50 for containing the liquid. By way of example, the reservoir 50 may be large enough to contain a volume of liquid sufficient to fill and maintain liquid circulation through at least one interconnectable patient heat exchange device(s), such as a patient contact pad(s).

Figure 7:
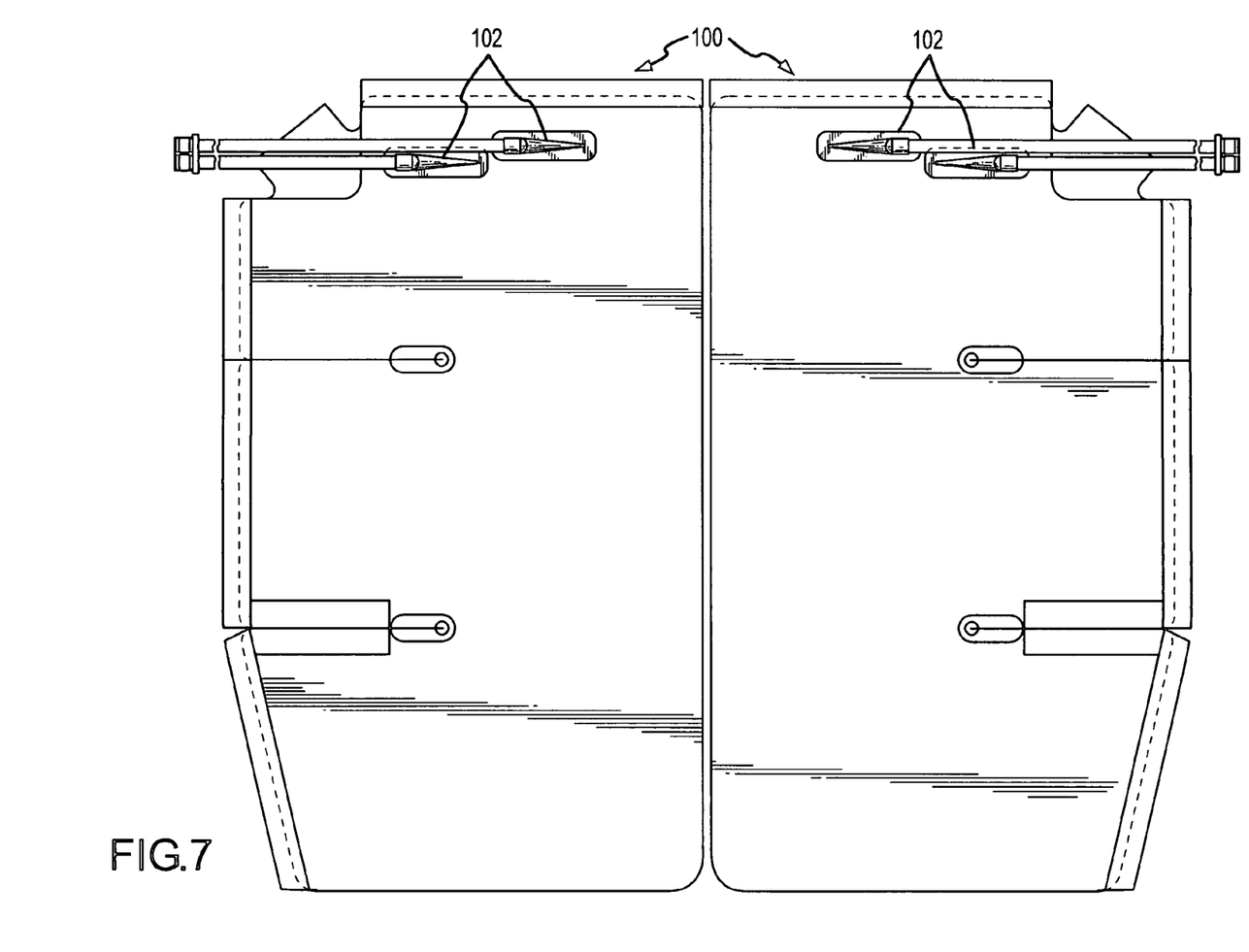
FIG. 7 illustrates an exemplary patient contact pad set for contacting a patient.

In the later regard, FIG. 7 illustrates an exemplary patient contact pad set 100 for contacting a right and left side of a patient. Patient contact pads 100 each have liquid inlet and outlet ports 102 for receiving/returning liquid from/to portable apparatus 10. The circulated liquid flows through a liquid circulation layer at each of the pads 100. In turn, an adhesive layer (e.g. defined by a hydrogenal layer may be adhered to a patient's skin to affect heat transfer. In one arrangement, release liners may be provided on the adhesive surface of the pads and readily removed prior to use. Pads of this nature, enlarged so as to contact both the abdomen and thighs of a patient, are offered by Medivance Incorporated of Louisville, Colo., model/catalog number 000316-03 (small), -07 (medium) or -09 (large). Such pad sets provide for direct surface contact and heat exchange with between about 25% to 40% of a patient's surface area.

Referring again to FIG. 2, reservoir 50 may be sized to contain an amount of liquid of at least about 1.2 liters, and preferably between about 1.2 liters and 2.0 liters. Such liquid amount allows for filling and continuously circulating cooled fluid through a set of patient contact pads of the type noted above.

As further shown in FIG. 2, the portable apparatus 10 includes a refrigerator 60 for circulating a cooling refrigerant through heat exchanger 30. By way of example, a freon refrigerant may be employed. Additionally, a power storage supply 70 is included for providing stand-alone electrical power to the various componentry of the apparatus, including circulating pump 20, refrigerator 60, user interface 20 and additional parameter sensing, processing and circuit componentry. The portable apparatus 10 may also include a power cord (not shown) for interfacing with an external electrical power source (e.g. a standard wall power outlet and/or emergency vehicle alternator). In this regard, the portable apparatus 10 may be adapted to operate with external electrical power sources that can supply at least a 3 amperes current at 115VAC (e.g. for operation of componentry other than heater 40), and more preferably, at least about a 6 amperes current at 115VAC (e.g. for operation of all componentry).

Figure 4:
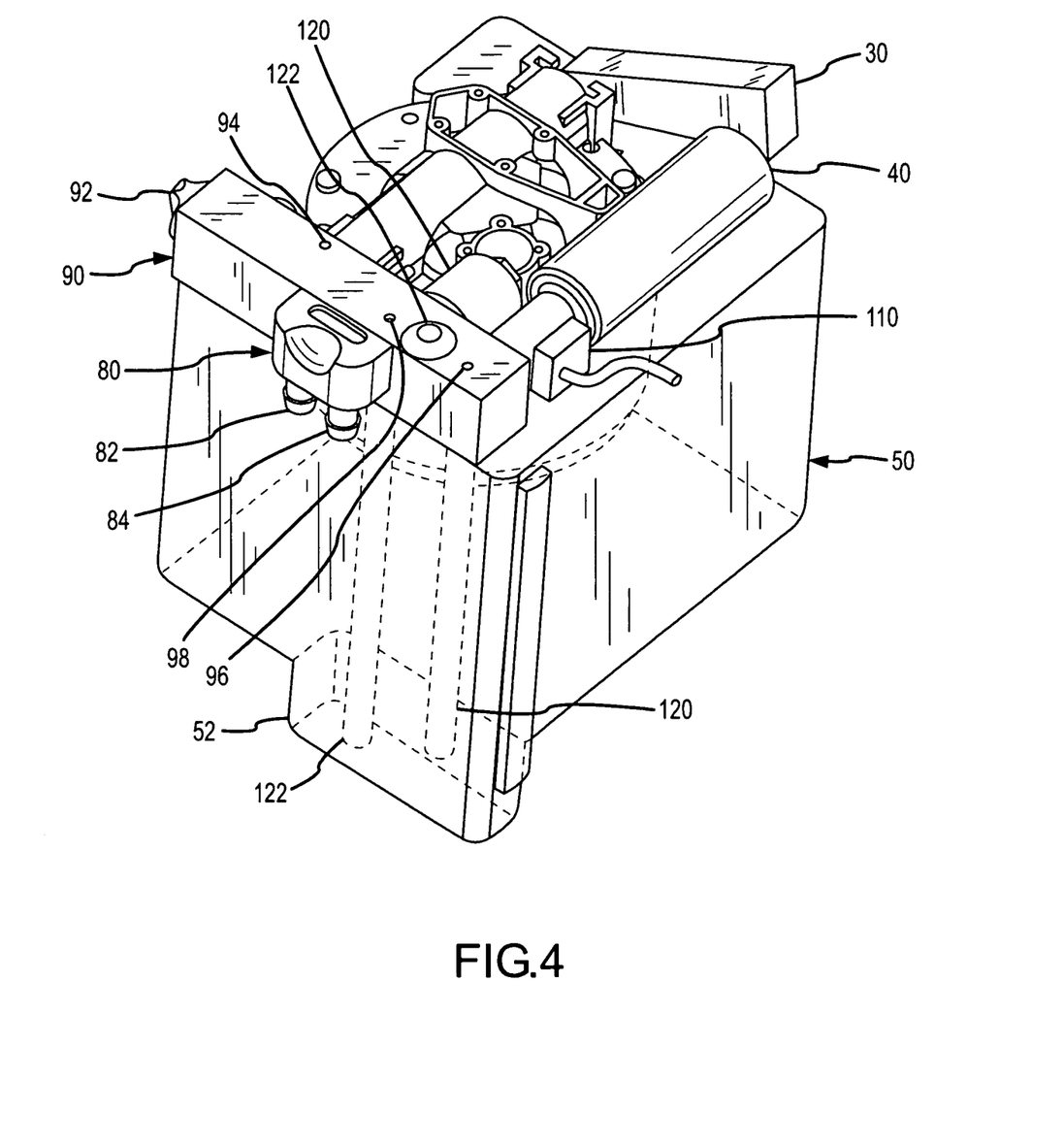
FIG. 4 is a perspective view of liquid cooling circuit componentry of the portable apparatus embodiment shown in FIG. 2.

FIGS. 2, 3 and 4 will now be referenced for further description of the liquid circulation circuit and additional related componentry of the portable apparatus 10. As shown, a manifold 80 may be provided that includes a liquid inlet port 82 and liquid outlet port 84 for selective interconnection to connector components utilized for the return and supply of liquid circulated to at least one interconnectable patient contact pad(s). In this regard, connector assemblies may be employed as taught in U.S. Pat. Nos. 6,827,728 and 6,802,855 referenced above, and an interconnectable patient contact pad(s) may be employed as disclosed in U.S. Pat. Nos. 6,375,674 and 6,669,715 referenced above.

During use of portable apparatus 10, the operation of circulating pump 20 serves to establish a negative pressure in the interconnectable patient contact pad(s), so as to draw the circulated liquid through inlet port 82. The circulated liquid then passes through an internal passageway of block 90 and into the circulating pump 20. An inlet liquid filter 92 may be disposed within block 90 to filter the circulated liquid. The filter 92 may be accessed via a removable cap 92 for maintenance. Further, cap 92 may be removed for selective introduction of liquid as may be needed from time to time.

As shown in FIG. 3, a return temperature sensor 102 may be provided to sense the temperature of the liquid returning from an interconnectable patient contact pad(s) and provide an output signal relating thereto. Such output signal may be provided to a processor for use in the control of the apparatus 10, including for example control over the speed of circulating pump 20 and operation of heater 40. The return temperature sensor 102 may be disposed within a port 94 of block 90 so as to access to the internal liquid passageway.

Upon passage of the liquid through circulating pump 20, the liquid is pumped through the heat exchanger 30, heater 40 and into reservoir 50. As will be appreciated, the location of such componentry downstream of the circulating pump 20 enhances operation of the portable apparatus 10. For example, the pressure drop between the circulating pump 20 and the patient contact pad(s) fluidly interconnected upstream thereof may be reduced.

As schematically shown in FIG. 3, heat exchanger 30 provides for the passage of the circulated liquid through a first passageway that is in contact relation with a second passageway extending therethrough, thereby providing for thermal exchange therebetween. In this regard, refrigerator 60 provides for the cooling and circulation of the refrigerant through the second passageway of heat exchanger 30.

As noted, liquid circulated through heat exchanger 30 may be heated by heater 40. Specifically, the heater 40 is provided to yield rapid and precise temperature adjustment control over the circulated liquid. In this regard, the operation of heater 40 may be controlled by a signal processor to yield desired patient cooling. In one example, heater 40 may comprise a resistive electrical heating element that is wound in a helical fashion about a conductive liquid passageway therethrough. In another arrangement, a conductive, helical liquid passageway may extend about a linear resistive, electrical heating element.

A flow meter 110 is provided downstream of heater 40 to sense the flow rate of the circulated liquid and provide an output signal relating thereto. Such output signal may be utilized by a processor in controlling operation of the apparatus 10, including in particular the speed of circulating pump 20 (e.g. to yield a desired flow rate and patient cooling rate).

As further shown in FIG. 3, liquid passing through heater 40 is pumped into the reservoir 50, then drawn out of reservoir 50 for supply to the interconnectable patient contact pad(s) via the outlet port 84 shown in FIG. 4. A control temperature sensor 104 and monitor temperature sensor 106 are provided to sense the temperature of liquid flowing into and out of the reservoir 50, respectively, and to provide corresponding output signals relating thereto. Such output signals may be provided to a processor for use in the control of portable apparatus 10, including in particular, the speed of circulating pump 20 and operation of heater 40. Temperature sensors 104 and 106 may be disposed in access ports 96 and 98 of block 90, respectively, so as to access corresponding internal passageways of block 90 through which the circulated liquid enters and exits reservoir 50, respectively. In the latter regard, inlet tube 120 and outlet tube 122 may be fluidly interconnected at their top ends to such internal passageways of block 90 and extend downward in reservoir 50 to introduce and remove liquid, respectively. As shown, reservoir 50 may comprise a bottom well portion 52 of a reduced size so as to collect liquid. In turn, the bottom end of outlet tube 122 may extend into the bottom well portion 52. A level sensor 130 may be utilized at reservoir 50 to sense the liquid level therewithin and provide an output signal relating thereto. Such output signal may be employed by a processor in operation of the portable apparatus (e.g. to provide an output at user interface 20 to indicate low liquid level conditions and/or to automatically suspend operations).

A vent valve 120 and air inlet 122 may also be provided at block 90 in communication with reservoir 50 through an internal passageway of block 90. In this regard, vent valve 120 provides for venting of the reservoir 50. More particularly, such venting allows reservoir 50 to be maintained at atmosphere pressure.

Referring now to FIGS. 2, 3, 5 and 6, refrigerator 60 will be further described. As illustrated, refrigerator 60 comprises a pair of high-speed, small displacement compressors 62a, 62b, a corresponding pair of condensers 64a, 64b (e.g. fin and tube type condensers), an expansion valve 66, and a fan 68. As will be appreciated, a single compressor and condenser may be utilized in other embodiments.

Figure 5:
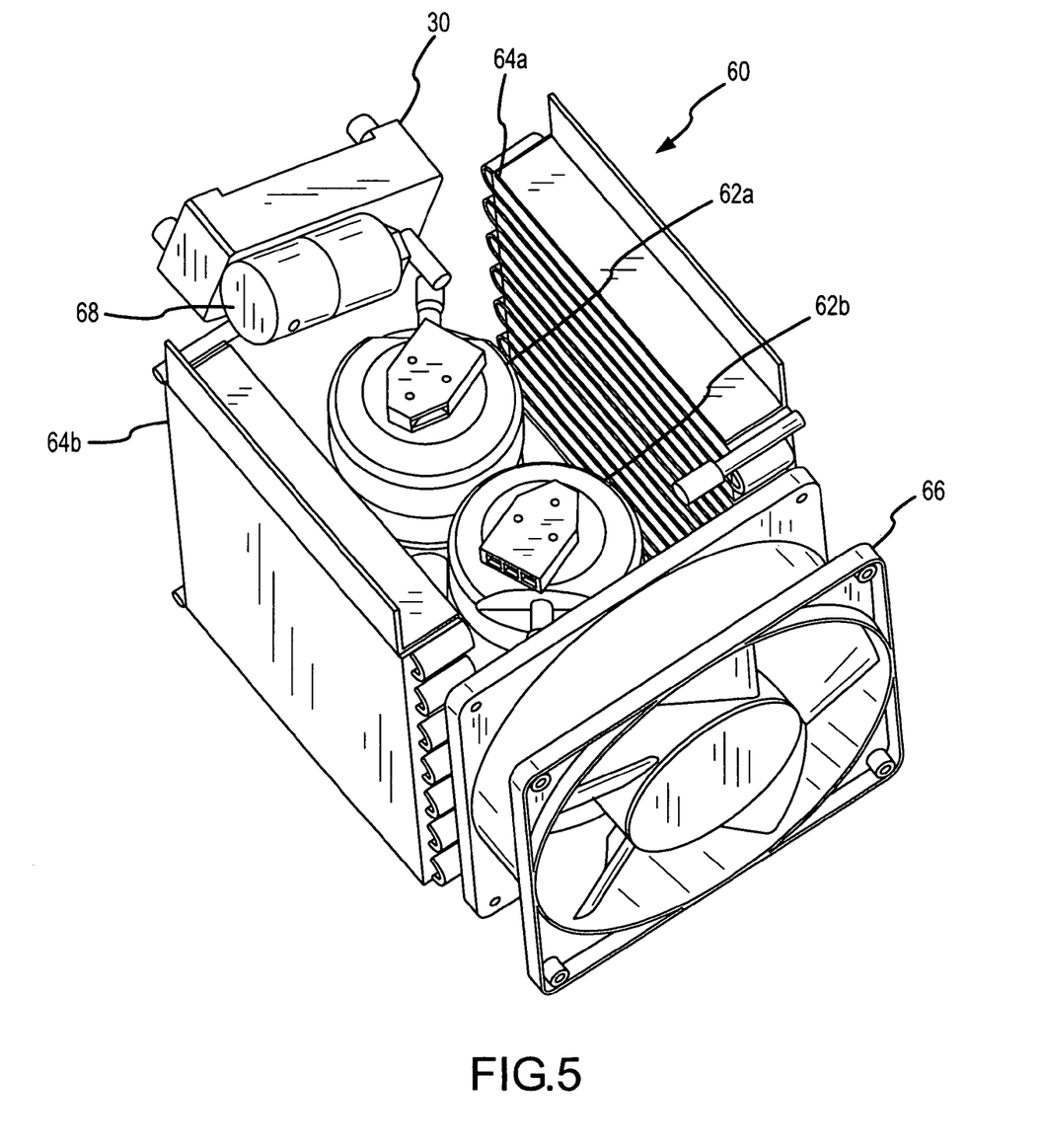
FIGS. 5 and 6 are perspective views of refrigerant circuit componentry of the portable apparatus embodiment illustrated in FIG. 2.
Figure 6:
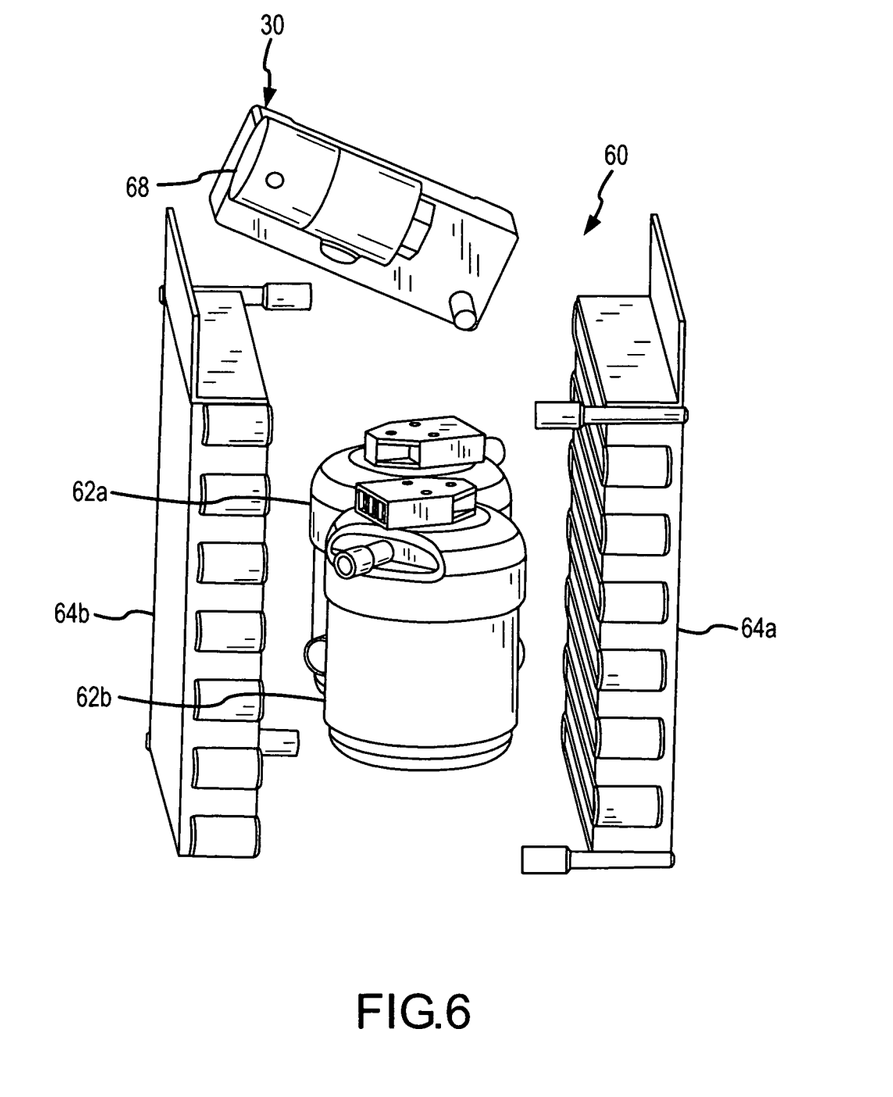

In operation of refrigerator 60, the refrigerant may be circulated by compressors 62a, 62b in a liquid form through condensers 64a, 64b, wherein the refrigerant is cooled by the passage of ambient air past condensers 64a, 64b by fan 66. Thereafter, the cooled refrigerant passes through expansion valve 68 and through heat exchanger 30 for heat exchange with the liquid that is circulated to the interconnectable patient contact pad(s).

As shown in FIG. 5, condensers 64a, 64b may be disposed on opposing sides at one end of the portable apparatus 10, and fan 66 may be disposed at the same end of portable apparatus 10 so as to direct ambient air into the space between the condensers 64a, 64b. In turn, such ambient air may pass through the condensers 64a, 64b and outward through side openings provided in the bottom housing 12, as shown in FIG. 1. Such an arrangement provides a compact and highly efficient refrigerator 60.

To enhance compactness, it may be noted that circulating pump 20 is located in a recess at the top of reservoir 50. More particularly, and as shown by phantom lines in FIGS. 2 and 4, the recess may be conformably shaped to mattingly receive the circulating pump 20.

To further enhance compactness it should be noted that the various components through which the circulated liquid passes are located in an immediately adjacent manner. That is, block 90 the inlet and outlet ports of circulating pump 20, heat exchanger 30, heater 40, and the inlet and outlet ports to reservoir 50 are disposed in an adjacent fashion, wherein a loop configuration is defined.

As shown in FIG. 2, the power storage supply 70 may comprise three storage modules 72 which each house a plurality of batteries 74. In this regard, any one of the modules 72 may be separately removed for battery replacement or recharge, while maintaining the operability of the apparatus 10 utilizing the power stored in one or both of the remaining modules 72. The power storage supply 70 is located across the bottom of the portable apparatus 10 thereby yielding space-savings and stability advantages. Preferably, the power storage supply 70 is capable of independently powering the portable apparatus 10 for between at least 20 minutes and 90 minutes, and more preferably between about 30 minutes and 60 minutes in stand-alone operation. In one arrangement, storage modules 72 may each comprise seven $LiMn_2O_4$ battery cells. Each of said battery cells has a cell capacity of about 3.5 Ah at 12A. In such arrangement, the power storage supply 70 can independently power the apparatus 10 for 60 minutes of stand-alone operation.

Referring to FIGS. 1 and 2, a number of observations should be made regarding the portable apparatus 10. First, it can be seen that the total volume of portable apparatus 10 is defined by a bottom layer A, an intermediate layer B, fluid circulation layer C and a top layer D. In this regard, the power storage supply 70 is located within and substantially fills the bottom layer A. The reservoir 50 and refrigerator 60 are located in side-by-side relation within intermediate layer B. Further, the nested portion of circulating pump 20 is located in intermediate layer B. The inlet and outlet ports of circulating pump 20 and reservoir 50, as well as the heat exchanger 30, heater 40 and block 90 all lie within the fluid circulation layer C, and. Such an arrangement yields a compact, portable apparatus 10.

More particularly, portable apparatus 10 may define a total volume of less than about 0.04 $m^3$, and more preferably between about 0.01 $m^3$ and 0.02 $m^3$. In relation to such a total volume, bottom layer A preferably defines between about 8% and 12% thereof (e.g. 11% in one arrangement), intermediate layer B preferably defines between about 50% and 70% thereof (e.g. 59% in one arrangement), fluid circulation layer C preferably defines between about 10% and 20% thereof (e.g. 15% in one arrangement) and the top layer D preferably defines between about 10% and 20% thereof (e.g. 15% in one arrangement).

Utilizing the described arrangement, a maximum width W of portable apparatus 10 may be less than about 9 inches and more preferably less than about 7 inches (e.g. about 6.5 inches in one arrangement). Further, a maximum height H of portable apparatus 10 may be maintained at less than between about 15 inches (e.g. about 11 inches in one arrangement). Additionally, a maximum length L of portable apparatus 10 may be maintained at less than about 16 inches, (e.g. about 14 inches in one arrangement).

As may be appreciated, the described sizing features facilitate use of portable apparatus 10 in emergency patient transport vehicles. For example, the portable apparatus 10 may be readily positioned adjacent to a patient gurney within a helicopter, ambulance or the like, wherein medical personnel may still work adjacent to or even over the portable apparatus 10.

In addition to the foregoing, the described arrangement also provides a relatively low-weight portable apparatus 10. In particular, portable apparatus 10 may have a total weight of less than about 15 kg., and more preferably between about 7 kg. and 12 kg. In this regard, such weight may be achievable with reservoir 50 containing at least about 1.2 liters of liquid (e.g. at least 1.2 kg. of water), and preferably between about 1.2 liters and 2.0 liters of water during non-use of the portable apparatus 10. Further the noted weight may be realized with batteries 74 having a total weight of less than about 3.5 kg., and preferably between about 1.17 kg. and 2.34 kg.

Figure 8:
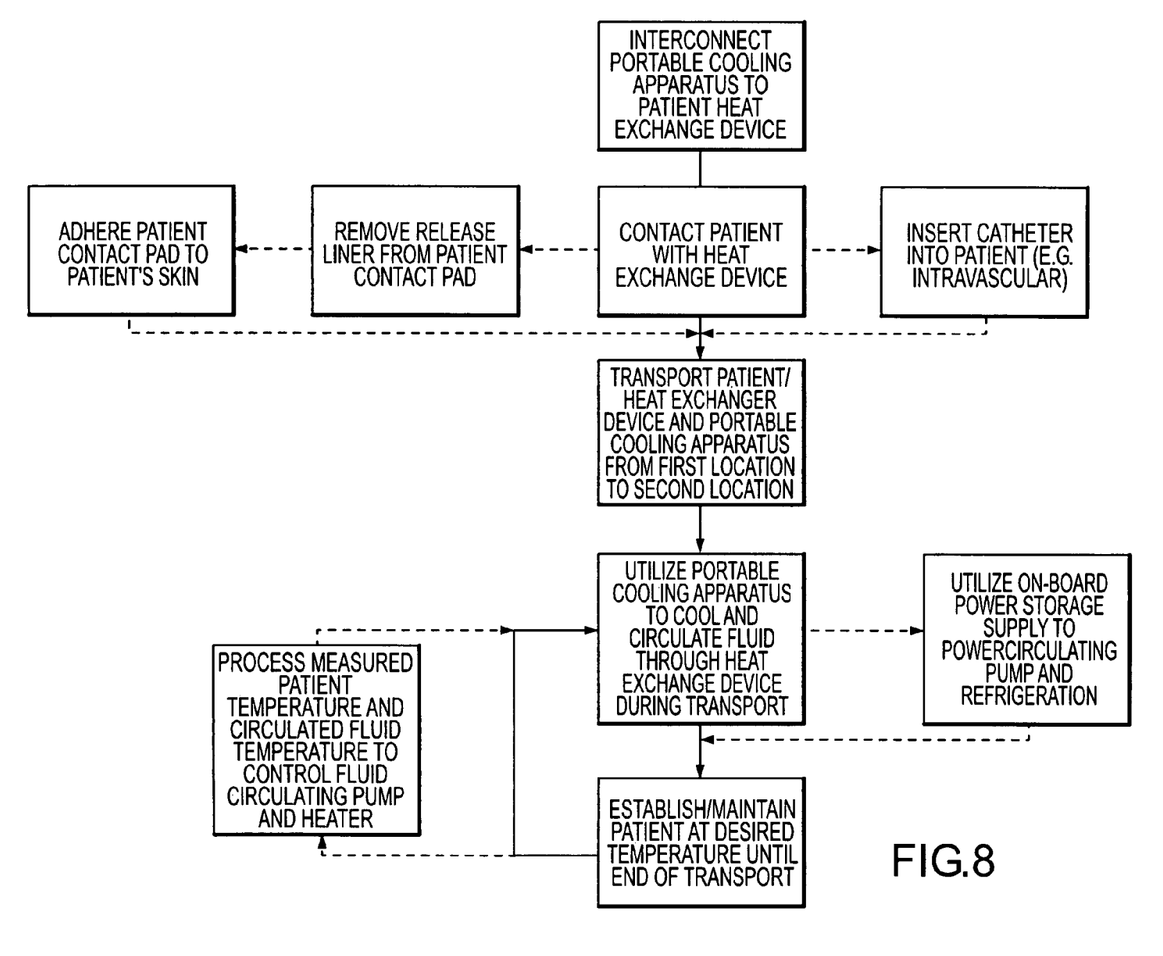
FIG. 8 illustrates steps of one embodiment at an inventive method.

Reference is now made to FIG. 8, which illustrates steps of one embodiment of an inventive method according to the present invention. In the illustrated embodiment, the above-described portable apparatus 10 is initially fluidly interconnected to patient heat exchange device, e.g. the patient contact pads shown in FIG. 7. In turn, a patient may be contacted with the heat exchange device. For example, when one or more patient contact pads are utilized, a release liner may be removed from an adhesive surface on the pad(s), and the pad(s) may be adhered to the skin of patient. Where the patient heat exchange device comprises an intravascular catheter, patient contact may established by inserting the catheter into the patient for contact with bodily fluid and/or bodily tissue of the patient.

As may be appreciated, in the illustrated embodiment the patient heat exchange device and portable cooling apparatus may be transported with the patient from a first location to a second location, and while utilizing the portable cooling apparatus to cool and circulate fluid through the heat exchange device. By way of example, in situations involving head trauma, cardiac arrest or stroke, emergency personnel may establish patient contact and initiate patient cooling at an emergency site. Then, the patient may be removed from the patient site utilizing a gurney while being cooled via the described arrangement. Next, the patient may be positioned into an emergency transport vehicle, e.g. an ambulance or helicopter, for transport to a medical care facility. Again, each of the transport stages may be completed while the patient is being rapidly cooled via a heat exchange device and portable cooling apparatus that travels with the patient.

In this regard, the inventive method may provide for the utilization of a power storage supply 70 comprising the portable cooling apparatus 60 in a stand-alone fashion to power a circulating pump 20 and refrigerator 60 of the portable cooling apparatus 10. As illustrated in FIG. 8, the portable cooling apparatus 10 may be employed to establish and maintain the patient at a desired temperature throughout the transport procedure. In arrangements where a refrigerator 60 is utilized to provide a constant rate of the fluid cooling, fine temperature adjustment may be achieved utilizing a heater 40 as described above. More particularly, a temperature sensor, such as temperature sensors 104 or 106 noted above may be utilized together with a measured patient temperature signal to control operation of a circulating pump 20 and heater 40. As may be appreciated, the circulating pump 20 may be operated at a speed which is appropriate to achieve a desired cooling effect. Similarly, heater 40 may be controlled at a heating level appropriate to achieve the desired cooling effect.

As may be appreciated various extensions, adaptations and modifications of the described portable apparatus 10 and described method embodiment may be made and are intended to be within the scope of the present invention, as defined by the claims that follow.

What is claimed is:

1. A portable apparatus for circulating a cooled fluid through at least one interconnectable patient heat exchange device, comprising:
   a reservoir for containing a fluid;
   a circulating pump, fluidly interconnected to said reservoir for portable movement therewith, for circulating said fluid;
   a heat exchanger, fluidly interconnected with said circulating pump and said reservoir for portable movement therewith, for cooling said circulatable fluid;
   a self-contained refrigerator, fluidly interconnected with said heat exchanger for portable movement therewith, for circulating a refrigerant through said heat exchanger to effect cooling of said circulatable fluid;
   a power storage supply, electrically interconnected to said circulating pump and said refrigerator for portable movement therewith, for storing and providing electrical power to electrically power operation of said circulating pump and to electrically power operation of said refrigerator during stand-alone, independent operation of said portable apparatus, free from interconnection of said heat exchanger and said self-contained refrigerator of said portable apparatus with an external electrical energy source; and,
   a patient heat exchange device for external patient contact and fluidly interconnectable to said circulating pump, wherein said fluid is circulatable therethrough by said circulating pump during said stand-alone, independent operation of said portable apparatus.

2. A portable apparatus as recited in claim 1, wherein said portable apparatus has a circulatable fluid cooling capacity of at least about 200 watts during said stand-alone, independent operation.

3. A portable apparatus as recited in claim 2, wherein said apparatus has a circulated fluid cooling capacity of between about 300 watts and 600 watts during said stand-alone, independent operation.

4. A portable apparatus as recited in claim 1, wherein said patient heat exchange device comprises:
   at least one patient contact pad for externally contacting a patient, wherein said fluid is a liquid that is circulatable through said at least one patient contact pad to cool a patient at a rate of at least about 1.0 C/hr during said stand-alone, independent operation.

5. A portable apparatus as recited in claim 1, further comprising:
   an external housing, wherein said external housing contains said reservoir, circulating pump, heat exchanger, self-contained refrigerator and power storage supply.

6. A portable apparatus as recited in claim 1, further comprising:
   a bottom housing and a top panel, wherein said reservoir, circulating pump, heat exchanger, self-contained refrigerator and power storage supply are at least partially disposed between said bottom housing and said top panel.

7. A portable apparatus as recited in claim 1, further comprising:
   an external housing, wherein said apparatus defines a total volume, wherein said total volume comprises a bottom layer and an intermediate layer overlying said bottom layer, wherein said refrigerator is located in said intermediate layer, and wherein said intermediate layer is contained within said external housing.

8. A portable apparatus as recited in claim 7, wherein said reservoir is located in said intermediate layer.

9. A portable apparatus as recited in claim 1, wherein said power storage supply comprises:
   at least one battery.

10. A portable apparatus as recited in claim 9, wherein said at least one battery is rechargeable.

11. A portable apparatus as recited in claim 1, wherein said power storage supply comprises:
   a plurality of rechargeable and replaceable batteries.

12. A portable apparatus for circulating a cooled fluid through at least one interconnectable patient heat exchange pad, comprising:
   a reservoir for containing a fluid;
   a circulating pump, fluidly interconnected to said reservoir for portable movement therewith, for circulating said fluid;

a heat exchanger, fluidly interconnected with said circulating pump and said reservoir for portable movement therewith, for cooling said circulatable fluid;

a self-contained refrigerator, fluidly interconnected with said heat exchanger for portable movement therewith, for circulating a refrigerant through said heat exchanger to effect cooling of said circulatable fluid;

a power storage supply, electrically interconnected to said circulating pump and said refrigerator for portable movement therewith, for providing electrical power to electrically power operation of said circulating pump and to electrically power operation of said self-contained refrigerator during stand-alone, independent operation of said portable apparatus, free from interconnection of said heat exchanger and said self-contained refrigerator of said portable apparatus with an external electrical energy source; and, a patient heat exchange pad fluidly interconnectable to the said circulating pump, wherein said fluid is circulatable through the patient heat exchange pad by said circulating pump during said stand-alone, independent operation, wherein said portable apparatus has a circulatable fluid cooling capacity of at least about 200 watts during said stand-alone, independent operation, and wherein said liquid is circulatable through said at least one patient heat exchange pad to cool a patient at a rate of between about 1.5 C/hr to 4.0 C/hr.

13. A portable apparatus as recited in claim 12, wherein said at least one patient heat exchange pad comprises:

a fluid circulation layer having an inlet port and an outlet port; and, an adhesive surface for contacting a patient's skin, wherein thermal exchange is provided through the adhesive surface.

14. A portable apparatus as recited in claim 12, wherein said circulating pump is fluidly interconnectable with said at least one patient heat exchange pad to circulate said liquid through said at least one patient heat exchange pad under negative pressure during said stand-alone, independent operation of said portable apparatus.

15. A portable apparatus as recited in claim 1, wherein said apparatus defines a total volume of less than about 0.04 m³, and wherein said total volume includes said reservoir, circulating pump, heat exchanger, self-contained refrigerator, and power storage supply.

16. A portable apparatus as recited in claim 15, wherein said apparatus defines a total volume of between about 0.01 m³ and 0.02 m³, and wherein said total volume includes said reservoir, circulating pump, heat exchanger, self-contained refrigerator, and power storage supply.

17. A portable apparatus as recited in claim 15, wherein said total volume has a maximum width dimension of less than about 9 inches.

18. A portable apparatus as recited in claim 17, wherein said total volume has a width of between about 4 and 7 inches, a height of between about 6 and 11 inches and a length of between about 9 and 14 inches.

19. A portable apparatus as recited in claim 15, wherein said power storage supply comprises less than about 12% of said total volume.

20. A portable apparatus as recited in claim 19, wherein said power supply comprises between about 8% and 12% of said total volume.

21. A portable apparatus as recited in claim 15, wherein said reservoir comprises less than about 16% of said total volume.

22. A portable apparatus as recited in claim 21, wherein said reservoir comprises between about 8% and 16% of said total volume.

23. A portable apparatus as recited in claim 15, wherein said power supply is located in a bottom layer of said total volume.

24. A portable apparatus as recited in claim 23, wherein said reservoir and said refrigerator are located in side-by-side relation in an intermediate layer of said total volume, said intermediate layer overlying said bottom layer.

25. A portable apparatus as recited in claim 24, wherein said heat exchanger is located in a fluid circulation layer of said total volume, said fluid circulation layer overlying said intermediate layer.

26. A portable apparatus as recited in claim 25, further comprising:

a flow meter, fluidly interconnected with said reservoir, circulating pump, and heat exchanger, for measuring a flow rate of said circulatable liquid and providing an output signal employable in controlling said circulating pump, wherein said flow meter is located in said fluid circulation layer.

27. A portable apparatus as recited in claim 26, wherein said power storage supply is operable to provide electrical power to said flow meter during stand-alone, independent operation of said portable apparatus.

28. A portable apparatus as recited in claim 25, further comprising:

a heater fluidly interconnected with said reservoir, circulating pump and heat exchanger, for heating said circulatable liquid, wherein said heater is located in said fluid circulation layer.

29. A portable apparatus as recited in claim 28, further comprising:

a first liquid temperature sensor located downstream of said heater and upstream of said at least one interconnectable patient heat exchange device, for sensing a temperature of said circulatable fluid and providing a first temperature signal relating thereto; and, a second liquid temperature sensor located upstream of said heater and downstream of said at least one interconnectable patient heat exchange device, for sensing a temperature of said circulatable fluid and providing a second temperature signal relating thereto, wherein at least one of said first and second temperature signals is employable in controlling at least one of the circulating pump and the heater.

30. A portable apparatus as recited in claim 28, wherein said power storage supply is operable to provide electrical power to said heater during stand-alone, independent operation of said portable apparatus.

31. A portable apparatus as recited in claim 25, wherein said refrigerator comprises:

at least one condenser;

at least one compressor for circulating the refrigerant through said at least one condenser and said heat exchanger; and, at least one fan for circulating ambient air past said at least one condenser.

32. A portable apparatus as recited in claim 31, wherein said refrigerator further comprises;

first and second condensers, wherein said first and second condensers are located along opposing first and second sides at one end of said apparatus, and wherein said at least one fan is located at said one end of the apparatus to circulate ambient air between and past said first and second condensers.

33. A portable apparatus as recited in claim 25, wherein said circulating pump is at least partially located within and supported within a top recess of said reservoir.

34. A portable apparatus as recited in claim 33, wherein said recess is shaped to substantially, conformably receive said circulating pump.

35. A portable apparatus as recited in claim 25, wherein said bottom layer defines between about 8% and 12% of said total volume, said intermediate layer defines between about 50% and 20% of said total volume, and said fluid circulation layer defines between about 10% and 20% of said total volume.

36. A portable apparatus as recited in claim 25, wherein said circulatable fluid is a liquid and wherein said apparatus has a total weight of less than about 15 kg with said reservoir containing at least about 1.2 liters of said liquid.

37. A portable apparatus as recited in claim 36, wherein said apparatus has a total weight of between about 7 kg and 12 kg with said reservoir containing between about 1.2 liters to 2.0 liters of said liquid.

38. A portable apparatus as recited in claim 37, wherein said apparatus has a circulatable fluid cooling capacity of at least about 0.005 watts/cm$^3$ at a weight of less than 0.375 g/cm$^3$.

39. A portable apparatus as recited in claim 38, wherein said apparatus has a circulatable fluid cooling capacity of between about 0.015 watts and 0.03 watts/cm$^3$ at a weight of between about 0.35 g/cm$^3$ and 0.6 g/cm$^3$.

40. A portable apparatus as recited in claim 25, wherein said circulating pump includes an inlet and an outlet located in said fluid circulation layer; and further comprising:
 a flow meter fluidly interconnected with said reservoir, circulating pump and heat exchanger, for measuring a flow rate of said circulatable liquid and providing an output signal employable in controlling said circulating pump, wherein said flow meter is located in said fluid circulation layer;
 a heater, fluidly interconnected with said reservoir, circulating pump and heat exchanger, for heating said circulatable liquid, wherein said heater is located in said fluid circulation layer, and wherein a fluid circulation pathway is defined by and between an inlet and outlet port of said circulating pump, said heat exchanger, said flow meter, said heater, and an inlet port and an outlet port of said reservoir, said fluid circulation pathway lying substantially entirely in said fluid circulation layer.

41. A portable apparatus as recited in claim 25, further comprising:
 at least one processor, electrically interconnected to said power storage supply, for controlling the operation of said circulating pump and said heater, said processor being located in a top layer overlying said fluid circulation layer; and,
 a user interface operatively interconnected with said processor for establishing control parameters applicable by said processor, said user interface being located in said top layer.

42. A portable apparatus as recited in claim 25, further comprising:
 an external housing, wherein said bottom, intermediate and fluid circulation layers are contained within said external housing.

43. A portable apparatus as recited in claim 24, further comprising:
 an external housing, wherein said intermediate layer is contained within said external housing.

44. A portable apparatus as recited in claim 12, wherein said power storage supply comprises:
 at least one battery.

45. A portable apparatus as recited in claim 44, wherein said at least one battery is rechargeable.

46. A portable apparatus as recited in claim 12, wherein said power storage supply comprises:
 a plurality of rechargeable and replaceable batteries.

* * * * *